United States Patent
Varghese et al.

(10) Patent No.: US 9,913,624 B2
(45) Date of Patent: Mar. 13, 2018

(54) METHOD AND APPARATUS FOR RAPID ACQUISITION OF ELASTICITY DATA IN THREE DIMENSIONS

(71) Applicant: Wisconsin Alumni Research Foundation, Madison, WI (US)

(72) Inventors: Tomy Varghese, Madison, WI (US); Atul Nishikant Ingle, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 273 days.

(21) Appl. No.: 13/780,880

(22) Filed: Feb. 28, 2013

(65) Prior Publication Data

US 2014/0243668 A1  Aug. 28, 2014

(51) Int. Cl.
*A61B 8/00* (2006.01)
*A61B 8/08* (2006.01)
*G01S 15/89* (2006.01)
*G01S 7/52* (2006.01)
*A61B 18/14* (2006.01)
*A61B 17/00* (2006.01)
(Continued)

(52) U.S. Cl.
CPC ............ *A61B 8/485* (2013.01); *A61B 8/4461* (2013.01); *A61B 8/4494* (2013.01); *A61B 18/1477* (2013.01); *G01S 7/52042* (2013.01); *G01S 15/894* (2013.01); *G01S 15/8918* (2013.01); *G01S 15/8925* (2013.01); *G01S 15/8979* (2013.01); *G01S 15/8993* (2013.01); *A61B 8/0841* (2013.01); *A61B 8/483* (2013.01); *A61B 2017/0011* (2013.01); *A61B 2018/0088* (2013.01); *A61B 2090/378* (2016.02)

(58) Field of Classification Search
CPC .. A61B 8/485; A61B 8/08; A61B 8/06; A61B 5/0048; A61B 8/0875
USPC .......................................... 600/407, 437–449
See application file for complete search history.

(56) References Cited

U.S. PATENT DOCUMENTS 4,341,120 A  7/1982  Anderson
5,159,931 A  11/1992  Pini
(Continued)

FOREIGN PATENT DOCUMENTS

KR  1020120107053 A  9/2012

OTHER PUBLICATIONS

Victor Torrealba, Antonio Bosnjak, Manuel Acuna, Lilia Hernandez Lilia, Christian Roux, Guillermo Montilla; 3D Dynamics echocardiography. Workstation for the acquisition, reconstruction and visualization of 4D images of the heart; 1er. Congreso Virtual de Cardiologia—Temas Libres Premiados—Torr . . . ; Publicacion Setiembre 2000; Webmaster—Actualization: 06-Ene-2005; p. 1-4; Venezuela.

(Continued)

*Primary Examiner* — Tse Chen
*Assistant Examiner* — Joanne Hoffman
(74) *Attorney, Agent, or Firm* — Boyle Fredrickson, SC (57) ABSTRACT

High-speed three-dimensional reconstruction of elasticity data is obtained by acquiring a sparse set of data in planes sharing a common axis line and angularly arrayed about the axis line. The axis line may be an RF ablation probe and the reconstruction may enforce a circumferential smoothness in the reconstruction about the probe, as is compatible with an ablation volume.

25 Claims, 4 Drawing Sheets

(51) Int. Cl.
*A61B 18/00* (2006.01)
*A61B 90/00* (2016.01)

(56) References Cited

U.S. PATENT DOCUMENTS

| | | | | |
|---|---|---|---|---|
| 5,485,842 A * | 1/1996 | Quistgaard | ............... | A61B 8/06 128/916 |
| 5,538,004 A * | 7/1996 | Bamber | ............... | G01S 7/52044 128/916 |
| 5,546,807 A * | 8/1996 | Oxaal | ................. | G01S 7/52034 73/602 |
| 6,228,028 B1 | 5/2001 | Klein et al. | | |
| 7,166,075 B2 * | 1/2007 | Varghese | ............... | A61B 5/015 600/407 |
| 7,302,092 B1 * | 11/2007 | Fenster | ............... | G01S 7/52034 382/128 |
| 9,307,953 B2 * | 4/2016 | Lee | ........................ | A61B 8/483 |
| 2005/0043619 A1 | 2/2005 | Sumanaweera et al. | | |
| 2005/0240170 A1 * | 10/2005 | Zhang | ............. | A61B 17/22012 606/27 |
| 2010/0137718 A1 * | 6/2010 | Pappalardo | ........... | B06B 1/0292 600/459 |
| 2010/0220895 A1 * | 9/2010 | Koren | .................... | G01V 1/345 382/109 |
| 2010/0240996 A1 | 9/2010 | Ionasec et al. | | |
| 2010/0256530 A1 * | 10/2010 | Varghese | ............... | A61B 5/015 600/587 |
| 2011/0295579 A1 * | 12/2011 | Tang | ....................... | A61B 6/466 703/9 |
| 2012/0128223 A1 | 5/2012 | Rivaz et al. | | |
| 2013/0004052 A1 | 1/2013 | Chen et al. | | |
| 2013/0150716 A1 * | 6/2013 | Stigall | .................... | A61B 6/504 600/439 |
| 2013/0177229 A1 * | 7/2013 | Inoue | ...................... | A61B 8/14 382/131 |

OTHER PUBLICATIONS

Internatonal Search Report; International application No. PCT/US2015/020943; Filing Date: Mar. 17, 2015.

* cited by examiner

METHOD AND APPARATUS FOR RAPID ACQUISITION OF ELASTICITY DATA IN THREE DIMENSIONS

STATEMENT REGARDING FEDERALLY SPONSORED RESEARCH

This invention was made with government support under CA112192 awarded by the National Institutes of Health. The government has certain rights in the invention.

CROSS-REFERENCE TO RELATED APPLICATIONS

BACKGROUND OF THE INVENTION

The present invention relates to ultrasonic imaging techniques for obtaining information about tissue elasticity and in particular to a method of rapidly acquiring three-dimensional elasticity reconstructions useful, for example, during RF ablation.

Elastography is an imaging modality that reveals the stiffness properties of tissues, for example axial strain, lateral strain, Poisson's ratio, Young's modulus, or other common stiffness measurements. The stiffness measurements may be output as quantitative values or mapped to a gray or color scale to form a picture over a plane or within a volume.

Generally, stiffness is deduced by monitoring tissue movement under an applied force or deformation. The monitoring may be done by any medical imaging modality including computed tomography (CT), magnetic resonance imaging (MRI), and ultrasonic imaging. Elastography of this type is analogous to a physician's palpation of tissue in which the physician determines stiffness by pressing the tissue and detecting the amount that the tissue yields under pressure.

In "dynamic" elastography, a low frequency vibration is induced in the tissue and the velocity of the resulting compression/shear waves is measured, for example, using ultrasonic Doppler detection. In "quasi-static" elastography, two images of the tissue are obtained at different states of compression, typically using the ultrasonic transducer as a compression paddle. Displacement of the tissue between the two images is used to deduce the stiffness of the tissue.

U.S. Pat. No. 7,166,072, assigned to the same assignee as the present invention and incorporated by reference, describes a novel technique for monitoring a radiofrequency ablation using quasi-static elastography. Radiofrequency or microwave ablation is a process for treating tumors or the like which employs one or more electrodes inserted percutaneously to the site of a tumor. Ionic heating of the tissue induced by radiofrequency fields in the tissue kills tumor cells and produces a hardened lesion. This lesion, being much stiffer than the surrounding tissue, may be monitored by quasi-static elastography using the ablation electrode as the compression device. Adhesion between the ablated tissue and the electrode allows the source of the compression to be at the site of the tumor (as opposed to external compression to the patient) providing a more accurate characterization of the stress field near the tumor and, accordingly, substantially improved elastographic measurement.

The present inventors have also developed a method of evaluating tissue elasticity by monitoring the propagation of shear waves extending generally perpendicularly to an axis of the ultrasound. The shear waves may be induced, for example, by reciprocation of an ablation probe. The speed of the shear wave is dependent on tissue elasticity, and may be extracted from the ultrasound image to reveal information about the size and growth of an ablated region. This process is described in U.S. Pat. No. 8,328,726 issued Dec. 11, 2012, assigned to the assignee of the present invention and hereby incorporated by reference.

Generally, these techniques may be used to produce three-dimensional elasticity data and images, for example, by sliding or rocking the ultrasound transducer to obtain multiple image planes within a volume. The data of these planes may be collected to produce a three-dimensional image. Substantial time is required to acquire the necessary data for these three-dimensional techniques limiting their usefulness for monitoring a real-time process such as RF ablation. Acquiring three-dimensional data sets is particularly time consuming when multiple registered images need to be obtained at each location as is often the case with elastography. Although data volumes can also be acquired directly using 2D ultrasound array transducers, the use of such technology is currently limited due to the high cost of manufacturing such sensor arrays.

SUMMARY OF THE INVENTION

The present invention provides a way of rapidly acquiring three-dimensional elasticity images by acquiring a limited number of planes of data extending along and arrayed angularly about a central axis. This acquisition technique allows, for example, monitoring of ablation on a real-time basis but may also be used for other 3-D imaging purposes. The radial acquisition pattern provides a good trade-off between reducing the required data acquisition while still providing the resolution necessary to identify ablation region boundaries or other similar volume edges.

Specifically then, the present invention may provide an apparatus for acquiring three-dimensional elasticity data having an ultrasonic probe assembly adapted to direct an ultrasound beam into an elastic material and receive ultrasonic echoes generally along an axis to acquire a set of planes of ultrasound data such that the axis lies substantially within each plane, and the planes are angularly spaced around the axis. An electronic computer receives the ultrasound data to compute measures of material elasticity at multiple points within each plane and reconstruct the multiple points of material elasticity of multiple planes into a three-dimensional representation of elasticity of the material.

It is thus a feature of at least one embodiment of the invention to provide a rapid 3-D acquisition and reconstruction system suitable, for example, for real-time monitoring of operations such as ablation. It is further a feature of at least one embodiment of the invention to provide an acquisition and 3-D reconstruction technique generally applicable to quantitative ultrasound imaging.

The set of planes may be between 4 and 6 in number.

It is thus a feature of at least one embodiment of the invention to reconstruct useful three-dimensional reconstructions with extremely sparse data.

The reconstruction of the multiple points of material elasticity of multiple planes may enforce a circumferential smoothness in the reconstruction.

It is thus a feature of at least one embodiment of the invention to provide an acquisition and reconstruction system well suited for structures that tend to be radially uniform about a known axis.

The reconstruction may employ a multidimensional interpolation (e.g., bilinear, trilinear or multilinear interpolation) along cylindrical coordinates centered on the axis.

It is thus a feature of at least one embodiment of the invention to provide a simple reconstruction algorithm providing one way to enforce circumferential smoothness.

The measures of material elasticity may evaluate speed of a shear wave extending perpendicularly through the material from the axis.

It is thus a feature of at least one embodiment of the invention to provide an acquisition and reconstruction system compatible with wave speed analyses of radially propagating shear waves.

The apparatus may further include an electrical probe adapted for percutaneous insertion into tissue at a tumor site communicating with a high-frequency power source to ablate tissue at the tumor site.

It is thus a feature of at least one embodiment of the invention to provide an ultrasound system for rapidly evaluating an ablated tumor volume on a real-time basis.

The electrical probe may include an actuator communicating with the electrical probe to provide reciprocation of the electrical probe along the axis.

It is thus a feature of at least one embodiment of the invention to provide a simple method of generating elasticity data well suited for the radial data acquisition pattern of the present invention.

The electronic computer may communicate with the actuator to time acquisitions of echoes to obtain multiple acquisitions of echoes at each of successive phase offsets with respect to a phase of the reciprocation of the electrode.

It is thus a feature of at least one embodiment of the invention to provide a method of evaluating shear wave propagation using B-mode data acquisition that would normally be too slow for such acquisition.

The measures of material elasticity may evaluate displacement of the material in response to a quasi-static periodic compression of the material.

It is thus a feature of at least one embodiment of the invention to provide an acquisition and 3-D reconstruction technique generally applicable to quasi-static elastography.

The ultrasonic probe assembly may be adapted to direct a tissue-stimulating beam of ultrasonic energy into the tissue to promote a displacement of the tissue measurable by the ultrasonic echoes, and wherein the measures of material elasticity evaluate the promoted displacement.

It is thus a feature of at least one embodiment of the invention to provide an acquisition and 3-D reconstruction technique generally applicable to dynamic elastography, for example acoustic radiation force impulse imaging (ARFI), Supersonic Shear Imaging (SSI), Electrode Vibration Elastography (EVE) and similar techniques.

The ultrasonic probe assembly may provide a substantially one-dimensional array of transducer elements extending perpendicularly to the axis and may provide a mechanism for rotating the one-dimensional array about the axis to acquire the multiple planes.

It is thus a feature of at least one embodiment of the invention to provide a simple acquisition system that may rotate a standard probe used for two-dimensional acquisitions.

Alternatively, the ultrasonic probe assembly may provide a two-dimensional array of transducer elements arrayed preferentially along lines of diameter extending perpendicular to the axis.

It is thus a feature of at least one embodiment of the invention to provide a specialized array for acquisition along multiple planes without necessary movement and compatible with limited acquisition bandwidth available in most ultrasound systems.

These particular objects and advantages may apply to only some embodiments falling within the claims, and thus do not define the scope of the invention.

DETAILED DESCRIPTION OF THE PREFERRED EMBODIMENT

General Description of the Hardware

Figures 1, 2, 3:
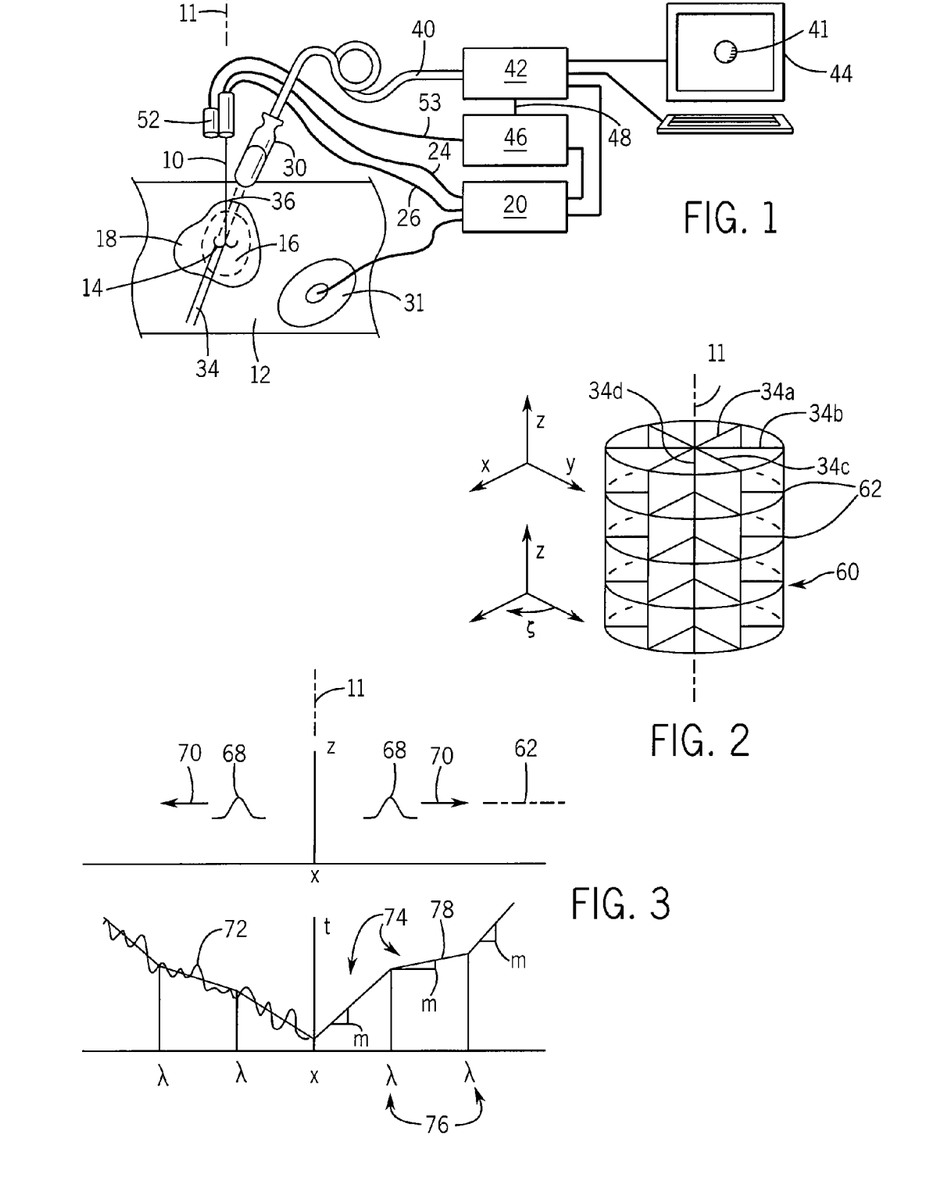
FIG. 1 is a simplified block diagram of an ultrasound imaging system for use with the present invention using a standard 2-D array ultrasound transducer as used with an optional RF ablation system providing an ablation probe for introduction into a tumor site of an in vivo organ and including a control system for applying a controlled reciprocation RF ablation probe for shear wave or quasi-static elastography imaging.
FIG. 2 is a simplified depiction of a geometry of a pattern of data acquisition employed in the present invention showing an example with four angularly separated planes of data acquisition sharing a common axis.
FIG. 3 is a graph of the shear wave propagation along an x-axis as fit to a set of constant slope segments by preprocessing/filtering/smoothing technique for noise reduction.

Referring now to FIG. 1, an RF ablation probe 10 may be inserted percutaneously into a patient 12 along an axis 11 to have its tip located at an ablation region 16 within an organ 18, such as the liver. Extensible electrode tines 14, at the tip of the probe 10, may grip the tissue of the ablation region and provide a greater area of electrical contact to conduct ablative current from a radiofrequency (RF) source 20.

In this regard, electrical energy from the RF source 20 is conducted through an insulated shaft of the probe 10 to the conductive tines 14 where ionic heating of the tissue kills tumor tissue. A large-area grounding pad 31 placed on the patient's skin provides a return path for this current. The tines 14 may optionally include thermocouples for temperature measurements used to control the electrical energy to minimize the formation of a layer of high impedance charred tissue between the tines 14 and the tissue.

RF ablation probes 10 suitable for this purpose may include a single 17-gauge electrode, with a 2-3 cm long electrically active region at the tip embedded in tissue. These electrodes also offer the option of internally circulating chilled water during the ablation procedure to minimize the charring of tissue adjacent to the electrically active region of the electrode. RF ablation probes 10 of this kind having extensible tines and thermocouple sensors are known in the art and commercially available, for example, under the tradename Valleylab Cool-Tip™ ablation electrode manufactured by Valleylab, Colo., USA, or from other companies. The RF source 20 may be a Rita Model 30 electrosurgical device manufactured by Rita Medical Systems, Inc., Mountain View, Calif., or another similar device.

During the ablation process, electrical current is conducted from the RF source 20 along line 26 to the ablation probe 10. The temperature signal is returned along line 24 to be received by the RF source 20 and used to limit the temperature of ablation according to techniques well understood in the art.

Imaging of the tissue and the tip of the probe 10 may be done using standard ultrasonic imaging system hardware, for example the Siemens S2000 Real Time Scanner manufactured by Siemens, Inc. of California. The ultrasonic imaging system hardware may include an ultrasonic transducer 30 communicating with ultrasound processing circuitry 42. The ultrasonic transducer 30 may be, for example, a one-dimensional ultrasonic transducer 30 (meaning that it has a one-dimensional array of individual transducer elements to acquire data over two dimensions) in the form of a linear array transducer approximately forty millimeters wide, operating with dynamic focus over a forty percent bandwidth and producing signals at a center frequency of five megahertz.

During insertion of the probe 10, the ultrasound transducer 30 is placed against the skin of the patient 12 to emit a beam 36 of ultrasound directed into the patient 12 to acquire echo data along an imaging or data plane 34 extending from the ultrasound transducer 30 (seen edgewise in FIG. 1). After insertion of the probe 10, the ultrasound transducer 30 may be used to monitor the ablation using elastographic imaging as will be described. During this monitoring and the subsequent elastographic imaging, the axis of the ultrasound transducer along which the ultrasound beam 36 propagates is aligned as closely as possible to the axis 11 along which the probe 10 extends. The probe 10 stabilizes the organ 18 and prevents lateral shifting along an axis perpendicular to axis 11.

During both insertion of the probe 10 and the ablation process, an ultrasound beam 36 generated by the ultrasound transducer 30 travels into the tissue of the patient 12 and is reflected at various tissue structures and boundaries. These echoes are detected by the ultrasound transducer 30 and conducted by cable 40 to the ultrasound processing circuitry 42. The received signals are digitized at a sampling rate of approximately 50 megahertz, and then processed according to techniques well known in the art, to produce a sequence of two-dimensional images, for example, providing a constantly refreshed B-mode image on display terminal 44.

A controller 46, which may be a computer or logic controller programmed as described below, may also provide output lines 53 connected to a motorized carriage 52, for example, using a motor and a lead screw (not shown) to provide motion of the probe 10 along its insertion axis 11 to reciprocate the probe 10 in a controlled manner according to signals on output line 53 as will also be described. Other mechanisms for implementing the motorized carriage 52, including those which apply a predetermined compressive force or low frequency oscillation, are also contemplated, for example, using an eccentric weight. In some embodiments, the controller 46 may also communicate with ultrasound processing circuitry 42 (or the display terminal 44 directly) for displaying images and receiving user input commands.

The digitized echo signals from the ultrasound transducer 30 are further processed either within the ultrasound processing circuitry 42, or within controller 46, to produce an elastographic image 41. In the former case, line 48 communicates signals from the controller 46 to the ultrasound processing circuitry 42 to coordinate generation of the elastographic image; in the latter case, line 48 carries the control signals and digitized echo signals from the ultrasound processing circuitry 42 to the controller 46 for processing by the controller 46.

Operation

Referring now to FIGS. 1 and 2, in a first embodiment, the ultrasound transducer 30 may be rotated about the probe 10 so as to rotate the data plane 34 about axis 11 while maintaining the plane 34 substantially aligned with axis 11. This rotation allows the acquisition of echo data along multiple planes. In this example four planes 34*a-d* are shown spaced from each other by 45 degrees. Other numbers of planes, for example five and six equally or unequally spaced planes 34, are also practical and there is generally no upper limit to the number of planes based on a trade-off between data acquisition and speed of reconstruction. Each of these planes 34 will provide multiple points of echo data over the surface of the plane 34, each point of echo data described, for example, by a z-axis coordinate value (where the z-axis is aligned with axis 11) and an x-axis coordinate value perpendicular to the z-axis and lying within the plane 34. Together the planes 34*a-d* are circumscribed within a cylindrical volume 60 that holds multiple C-planes 62 generally normal to axis 11 and spaced regularly along the z-axis. Generally, these planes may be acquired by beam steering or other techniques.

Figure 8:
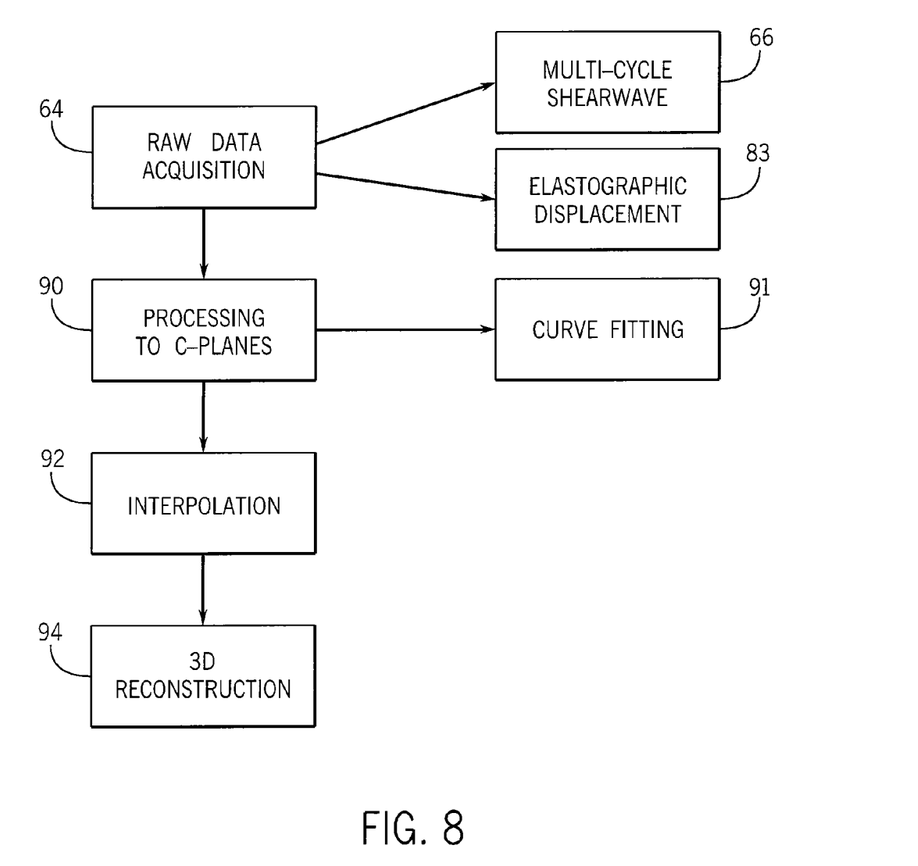
FIG. 8 is the principal steps of the present invention in several embodiments.

Referring momentarily to FIG. 8, in a first step of the invention, echo data of each plane 34 is processed to extract raw data necessary for elasticity measurements as indicated by process block 64. The deduced elasticity may indicate absolute or relative elasticity of the tissue, and the raw data may be obtained using various different techniques. In a first technique, indicated by sub process block 66, the data of the planes 34 may be processed to acquire multi-cycle shear wave data as will now be described.

Referring to FIGS. 1 and 3, a reciprocating motion of the probe 10, or other stimulation techniques such as ARFI, SSI and EVE and the like, may generate shear waves 68 propagating perpendicularly to axis 11, for example radially away from that axis 11 as indicated by arrows 70. Detection of the shear waves at each C-plane 62 may be performed by direct analysis of the radiofrequency ultrasonic signal or through the analysis of B-mode images to detect the displacement between successive images incident to the deformation of the shear wave 68, for example, as described in U.S. Pat. No. 8,328,726 cited above. Generally the generation of B-mode imaging will not occur rapidly enough to track movement of the shear waves 68 along arrows 70 in real time but an effective reconstruction of that motion may be obtained by coordination between ultrasound processing circuitry 42 and the controller 46 reciprocating the probe 10 to obtain data of the data plane 34 capturing the shear waves 68 at multiple times, each time having a different phase delay with respect to the reciprocation of the probe 10. Under the assumption that the shear waves 68 will be identical for each cycle of the reciprocation, this allows a piecewise reconstruction of the motion of the shear wave 68. Alternatively, the entire image plane can be scanned using a plane acoustic wave to bypass the low imaging speed of B-mode acquisitions. Such plane acoustic wave acquisitions image the complete imaging plane in a single sweep, unlike the sequential focused technique used in B-mode acquisitions.

As indicated by process block 90 of FIG. 8, propagation of the shear wave 68 in terms of arrival time at various locations along the x-axis may be plotted in a measurement curve 72 for each C-plane against different positions along the x-axis. The reciprocal of the slope of the measurement curve 72 will generally indicate the velocity of the shear wave 68 providing information about elasticity of the propagating medium. The substantial noise component in the measurement curve 72 presents a problem with respect to differentiating this measurement curve 72 in order to obtain velocity. Accordingly, the present invention first fits the measurement curve 72 to an a priori model of the tissue per process sub block 91. One such model postulates radially extending regions 74 of constant of propagation velocity having slopes m separated by breakpoints 76, for example, representing boundary lines between ablated tissue and unablated tissue within the organ or between unablated tissue within the organ and tissue outside of the organ, for example. By fitting this model 78 to the actual data of the measurement curve 72, velocities may be readily extracted as the values m with reduced noise. These velocities 1/m provide elasticity data for points in the data plane 34.

It will be appreciated that other methods of extracting data from the measurement curve 72 may be used, for example a stochastic hidden Markov model, wherein the hidden states of slopes and breakpoints are determined, for example, using a particle filter algorithm. See, for example, Arulampalam, M. S., Maskell, S., Gordon, N., Clapp, T., "A Tutorial on Particle Filters for Online Nonlinear/Non-Gaussian Bayesian Tracking,"Signal Processing, IEEE Transactions on, Volume 50, Number Two, Pages 174-188 (February 2002).

This process of fitting the measurement curve 72 to a model 78, for example, may provide a least square fit between the model 78 and the measurement curve 72 using standard numerical optimization routines such as sequential quadratic programming, interior point optimization, log-barrier algorithms, or stochastic optimization methods such as simulated annealing.

Figure 4:
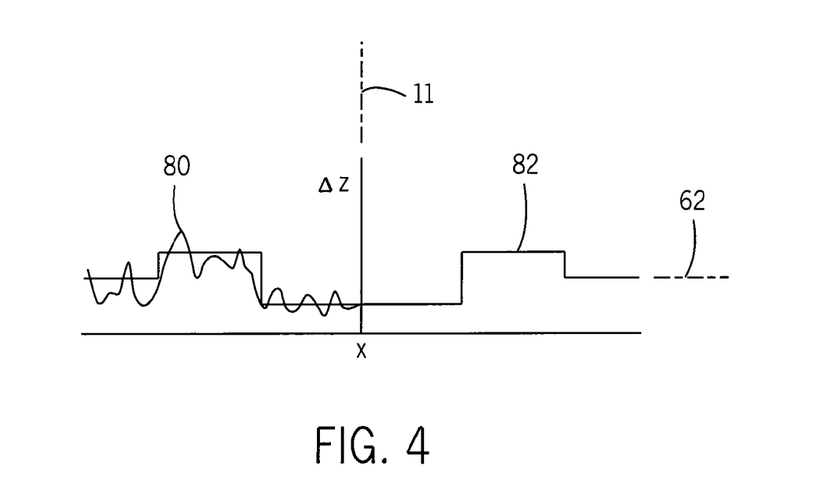
FIG. 4 is a graph similar to that of FIG. 3 showing tissue displacement at different points along the x-axis associated with quasi-static elastography.

Referring now to FIGS. 4 and 8, in an alternative technique, the acquired ultrasound data at process block 64 may be used to determine, at process block 90, z-axis displacement of the tissue with reciprocation of the probe along axis 11 or other stimulation of the tissue along axis 11; for example, ultrasonic stimulation, may be used to deduce tissue movement within a cycle of stimulation according to standard dynamic or quasi-static elastography. Again, a measurement curve 80 providing a measure along the x-axis for each C-plane 62 may be obtained and averaged or otherwise fit to a model 82 (e.g., multiple regions of constant elasticity) to obtain low noise signal from model 82 reflecting tissue elasticity per process sub block 83 of FIG. 8.

Figure 5:
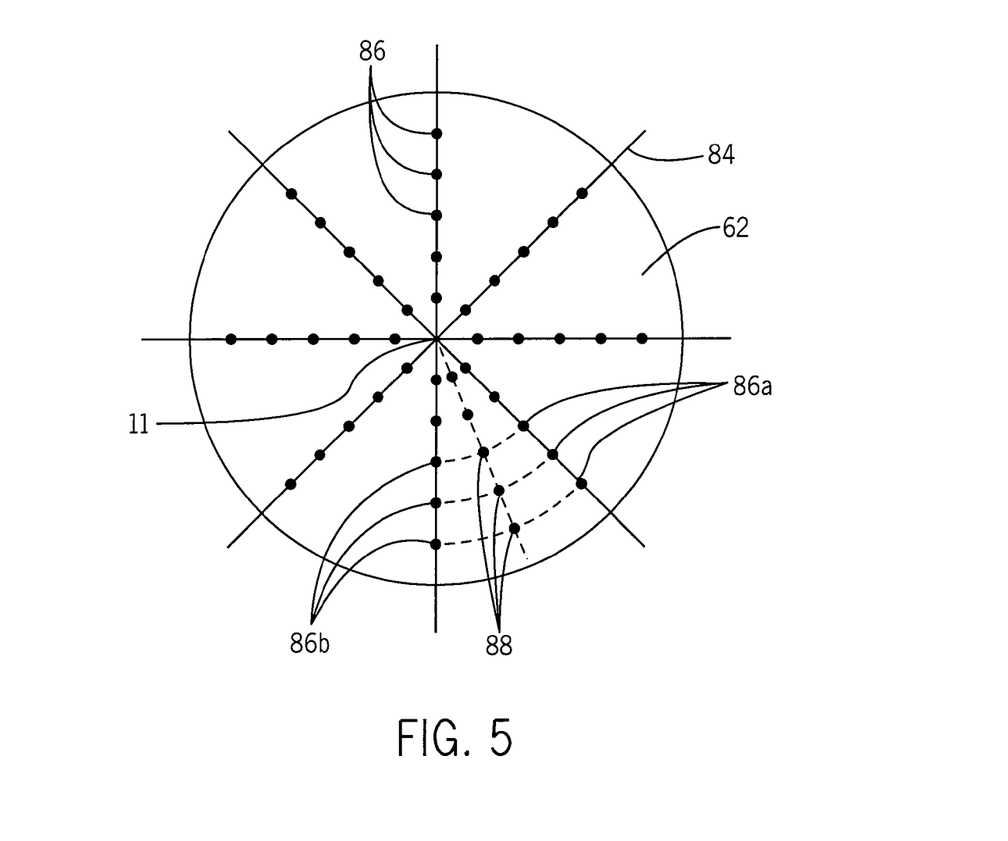
FIG. 5 is a top plan view of the data acquisition geometry of FIG. 2 showing bilinear cylindrical interpolation used in one embodiment of the invention.

Referring now to FIGS. 5 and 8, the data of model 78 or 82 acquired at process block 90 will lie along intersection lines 84 between the planes 34 and each C-plane 62 to provide for multiple elasticity data points 86 spaced along each of the lines 84 within each C-plane 62. This relatively sparse data may be interpolated, per process block 92 of FIG. 8, for example, to develop additional interpolated data points 88 between corresponding data points 86a and 86b of adjacent lines 84. This interpolation may use a bilinear or trilinear cylindrical interpolation (multidimensional or multilinear interpolation) where points 88 lie at a same radial distance from axis 11 as the corresponding points 86a and 86b from which they are interpolated. The trilinear interpolation operates between C-planes on corresponding points in each C-plane which may in turn be the result of bilinear interpolation. Additional interpolation between points 88 or between points 86a and 86b may also be performed. For convenience interpolated points 88 may be selected to lie on a rectilinear grid. It will be understood that normal Cartesian coordinates may also be used for interpolation in some embodiments.

It will be appreciated that this cylindrical interpolation enforces a circumferential smoothness to the data, that is, data that varies relatively smoothly as one moves in circumference about axis 11 at a given radius from axis 11. More generally, such circumferential smoothness may be implemented by using general numerical optimization techniques. For example, a nearest neighbor interpolation scheme may determine data values of unknown data for a vector x to be reasonably close to known data represented by vector b. The interpolator may be a matrix operator A which is a sparse matrix with very few nonzero values per row. In order to enforce circumferential and axial smoothness, it is assumed that the size of the gradient of the unknown vector x is small. This is enforced by adding the norm of the gradient into an objective function to be minimized by standard numerical optimization techniques such as those described above. Since the gradient for discrete data may be calculated by finite differencing, it can be expressed as Bx where B is the finite differencing matrix. A least squares optimization routine can then be used to solve for values of x to minimize:

$$\|Ax-b\|^2+\|Bx\|^2.$$

It will be appreciated that data can be acquired in multiple passes where the interpolated visualization from an earlier pass provide feedback for sampling interesting locations in the volume for subsequent passes to provide an adaptive sampling. In this respect, it will be further appreciated that data can also be acquired over beam planes 34 that are not angularly, uniformly spaced in order to derive better quality measurements from certain regions of the volume for finer interpolation reconstructions. Knowledge of earlier reconstructions can be easily incorporated in the interpolation procedure, for example, by reconstructing only a specific part of the volume that is known to contain an interesting feature or changed.

Upon filling in of the data of each C-plane 62 per the interpolation of process block 92, the data of each of the C-planes may be collected together to create a 3-D data set and to display an image 41 of the 3-D ablation zone, for example, as indicated by process block 94. This reconstruction may use conventional 3-D reconstruction and display techniques. For example, view of the ablation region 16 isolated from other surrounding tissue, for example of the organ 18, may be created by a sorting of the data by an elasticity threshold and creating a polygon defined surface from outermost points within that threshold.

Figure 6:
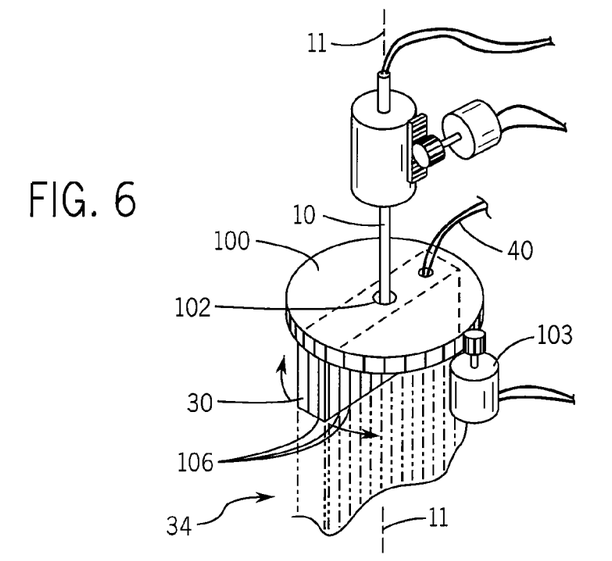
FIG. 6 is a simplified representation of an ultrasonic transducer for automatically acquiring data in the geometry shown in FIG. 2 by rotation of a 2-D ultrasound probe.

Referring now to FIG. 6, in one embodiment, movement of the ultrasonic transducer 30 may be automated by mounting a one-dimensional or 1.5 D ultrasonic transducer 30 on an axially reciprocating carriage 100, for example, driven by electric actuator 103 under the control of controller 46 (shown in FIG. 1). The transducer 30 may provide, for example, one (for a one-D probe) or a small number such as three rows of ultrasonic elements 106 (for a 1.5-D probe) each that may be separately actuated for phased array or other imaging modes to transmit portions of the ultrasound beam 36 and to be independently readable to receive echo signals in return. The multiple rows of ultrasonic elements help provide for focusing of the ultrasound into a substantially planar ultrasound beam 36. The reciprocating carriage 100 may rotate the ultrasonic transducer 30 about axis 11 substantially mimicking the motion described above with respect to FIG. 1 while providing improved orientation of the resulting ultrasound beam 36 along the axis 11. The reciprocating action, for example, may move the ultrasonic transducer 30 by 180 degrees in one direction and then backward to its initial starting position to obtain the sheaf of data planes 34 described with respect to FIG. 2. A center of the ultrasonic transducer 30 may provide for an opening 102 through which the probe 10 may pass to permit for this improved orientation of the ultrasound beams 36 with the axis 11 while sacrificing only one center ultrasonic element 106 of the ultrasonic transducer 30 in an area which is generally oversampled. A simplified motorized carriage 52 is shown providing for vertical reciprocation along axis 11 of the probe 10 also under control of controller 46.

Figure 7:
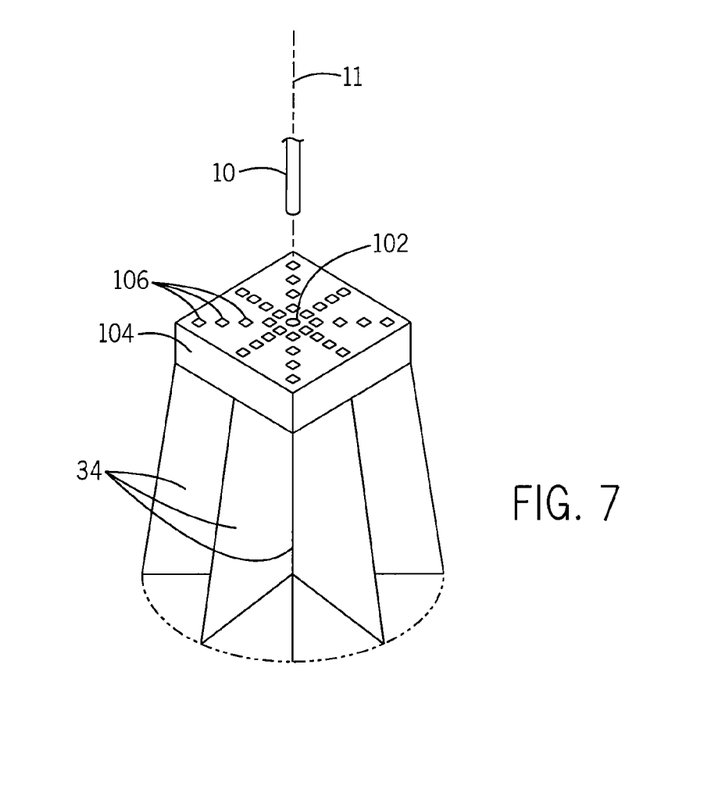
FIG. 7 is a figure similar to that of FIG. 6 showing a sparse 3-D ultrasonic probe for obtaining data in the geometry of FIG. 2.

Referring now to FIG. 7, in an alternative embodiment, a modified two-dimensional array 104 may be created having scattered ultrasonic elements 106 positioned as needed for the acquisition of the multiple planes 34 without movement of the two-dimensional array 104. For example, the ultrasonic elements 106 may be placed along diagonal lines arrayed radially from axis 11 with a 45-degree spacing. This sparse ultrasound array reduces the number of channels necessary for data acquisition while still providing the rapid 3-D reconstruction of the present invention.

It will be appreciated that the spacing of the ultrasonic elements 106 along the lines perpendicular to the axis 11 of the ultrasonic elements 106 may be varied, for example, to reduce the element density toward the center of the array in favor of those ultrasonic elements 106 further outward for improved imaging resolution away from the center. The array 104 may be combined with the reciprocating carriage 100 to create a hybrid system.

It will be appreciated that the present invention may be combined with techniques to measure temperature of an ablated region, for example, as described in U.S. Pat. No. 7,166,075 hereby incorporated by reference.

It will be appreciated that the present invention may be used advantageously with parametric imaging techniques on radiofrequency, or B-mode data for 3-D quantitative ultrasound imaging. In addition, the invention can be used with color/power Doppler systems, for example, to produce a three-dimensional representation of blood flow.

It will be further appreciated that the present invention may be used advantageously with standard imaging techniques such as B-mode, color and power Doppler imaging and the like for ablation techniques in which the simplification of the imaging acquisition provides for good reconstruction of ablation masses and for other high-speed 3-D visualization such as blood flow for 3-D vascular imaging.

It is specifically intended that the present invention not be limited to the embodiments and illustrations contained herein, but include modified forms of those embodiments including portions of the embodiments and combinations of elements of different embodiments as come within the scope of the following claims.

We claim:

1. An apparatus for acquiring three-dimensional elasticity data comprising:
   an electrical probe configured for percutaneous insertion into tissue at a tumor site to provide for the ablation of tissue in an ablation region growing radially from a proximal end of the electrical probe;
   an ultrasonic probe assembly configured to direct an ultrasound beam into an elastic material and receive ultrasonic echoes generally along an axis intersecting the ablation region to acquire data at corresponding points within a limited set of planes of ultrasound data within a cylindrical volume such that the axis lies within each plane, and the planes are angularly spaced around the axis without an acquisition of data between the planes; and
   an electronic computer receiving the ultrasound data and executing a stored program held in non-transitive medium to:
   (a) using corresponding points of echo data within each plane in the limited set of planes, interpolate points of echo data between planes in multiple C-planes normal to the axis to provide multiple points of echo data within each plane and between planes;
   (b) compute measures of material elasticity at the multiple points of echo data; and
   (c) reconstruct the multiple points of material elasticity of multiple planes and C-planes into a three-dimensional representation of elasticity of the material;
   wherein the interpolated points of echo data between planes in multiple C-planes normal to the axis are interpolated along cylindrical paths circumferentially around the axis to enforce a circumferential smoothness in the echo data, and
   wherein the measures of material elasticity evaluate speed of a shear wave extending perpendicularly through the material from the axis.

2. The apparatus of claim 1 wherein the set of planes is between four and six in number.

3. The apparatus of claim 1 wherein the reconstruction employs a trilinear multidimensional interpolation along cylindrical coordinates centered on the axis.

4. The apparatus of claim 1 wherein the electrical probe configured for percutaneous insertion into tissue at the tumor site further includes
   a power source communicating with an electrode of the electrical probe to ablate tissue at the tumor site, the power source providing a frequency selected from radiofrequency and microwave frequencies.

5. The apparatus of claim 4 further including an actuator communicating with the electrical probe to provide reciprocation of the electrical probe along the axis.

6. The apparatus of claim 5 wherein the electronic computer communicates with the actuator to time acquisitions of echoes to obtain multiple acquisitions of echoes at each of successive phase offsets with respect to a phase of the reciprocation of the electrode.

7. The apparatus of claim 1 wherein the measures of material elasticity evaluate displacement of the material in response to a quasi-static periodic compression of the material.

8. The apparatus of claim 1 wherein the ultrasonic probe assembly is further configured to direct a material-stimulating beam of ultrasonic energy into the material to promote a displacement of the tissue measurable by the ultrasonic echoes and wherein the measures of material elasticity evaluate the promoted displacement.

9. The apparatus of claim 1 wherein the ultrasonic probe assembly provides a one-dimensional array of transducer elements extending perpendicular to the axis and providing a mechanism for rotating the one-dimensional array about the axis to acquire the multiple planes.

10. The apparatus of claim 1 wherein the ultrasonic probe assembly provides a two-dimensional array of transducer elements arrayed preferentially along lines of a diameter extending perpendicular to the axis.

11. The apparatus of claim 1 wherein the electronic computer further executes the stored program to display a three-dimensional rendering of elasticity of the material.

12. A method of acquiring three-dimensional elasticity data comprising the steps of:
(a) inserting an electrical probe configured for percutaneous insertion into tissue at a tumor site to provide for the ablation of tissue in an ablation region growing radially from a proximal end of the electrical probe;
(b) applying a power source communicating with the electrical probe to ablate tissue at the tumor site;
(c) using an ultrasonic probe to direct an ultrasound beam into an elastic material and receive ultrasonic echoes generally along an axis intersecting the ablation region to acquire data at corresponding points within a limited set of planes of ultrasound data within a cylindrical volume such that the axis lies within each plane, and the planes are angularly spaced around the axis without an acquisition of data between the planes;
(d) using corresponding points of echo data within each plane in the limited set of planes, computing by interpolation points of echo data between planes in multiple C-planes normal to the axis to provide multiple points of echo data within each plane and between planes;
(e) computing measures of material elasticity at the multiple points of echo data; and
(f) reconstructing the multiple points of material elasticity of multiple planes and C-planes into a three-dimensional representation of elasticity of the material;
wherein the interpolated points of echo data between planes in multiple C-planes normal to the axis are interpolated along cylindrical paths circumferentially around the axis to enforce a circumferential smoothness in the echo data, and
wherein the measures of material elasticity evaluate speed of a shear wave extending perpendicularly through the material from the axis.

13. The method of claim 12 wherein the set of planes is between 4 and 6 in number.

14. The method of claim 12 wherein the reconstruction employs a trilinear multidimensional interpolation along cylindrical coordinates centered on the axis.

15. The method of claim 12 wherein the measures of material elasticity evaluate at least one of a speed of a shear wave extending perpendicularly through the material from the axis and a quasi-static periodic compression of the material.

16. The method of claim 12, wherein the steps of inserting the electrical probe into tissue at the tumor site and
applying the power source communicating with the electrical probe to ablate tissue at the tumor site further includes the power source providing a frequency selected from radiofrequency and microwave frequencies.

17. The method of claim 12 further including the step of displaying a three-dimensional rendering of elasticity of the material.

18. The method of claim 12 further including the step of applying a quasi-static compression to the material and wherein the measures of elasticity are computed from a determination of material displacement between different quasi-static compressions.

19. A method of acquiring three-dimensional elasticity data comprising the steps of:
(a) inserting an electrical probe configured for percutaneous insertion into tissue at a tumor site to provide for the ablation of tissue in an ablation region growing radially from a proximal end of the electrical probe;
(b) applying a power source communicating with the electrical probe to ablate tissue at the tumor site, the power source providing a frequency selected from radiofrequency and microwave frequencies;
(c) using an ultrasonic probe to direct an ultrasound beam into an elastic material and receive ultrasonic echoes generally along an axis intersecting the ablation region to acquire data at corresponding points within a limited set of planes of ultrasound data within a cylindrical volume such that the axis lies within each plane, and the planes are angularly spaced around the axis without an acquisition of data between the planes;
(d) using corresponding points of echo data within each plane in the limited set of planes, computing by interpolation points of echo data between planes in multiple C-planes normal to the axis to provide multiple points of echo data within each plane and between planes;
(e) computing measures of material elasticity at the multiple points of echo data; and
(f) reconstructing the multiple points of material elasticity of multiple planes and C-planes into a three-dimensional representation of elasticity of the material of the tumor site; and
wherein the interpolated points of echo data between planes in multiple C-planes normal to the axis are interpolated along cylindrical paths circumferentially around the axis to enforce a circumferential smoothness in the echo data, and
wherein the measures of material elasticity evaluate speed of a shear wave extending perpendicularly through the material from the axis.

20. The apparatus of claim 1, wherein the ultrasonic probe includes an array of ultrasonic transducers extending along a line generally perpendicularly to the axis and further including an opening in the ultrasonic probe assembly within the line, wherein the electrical probe passes through the opening.

21. The apparatus of claim 20, further including an actuator communicating with the electrical probe to provide reciprocation of the electrical probe along the axis.

22. The apparatus of claim 21, further including an actuator configured to provide rotation of the ultrasonic probe assembly about the axis.

23. The apparatus of claim 21, wherein the ultrasonic probe assembly provides a single linear array of transducer elements extending perpendicular to the axis and a mechanism for rotating the one-dimensional array about the axis to acquire the multiple planes.

24. The apparatus of claim 21, wherein the ultrasonic probe assembly provides first and second lines of transducer elements extending radially from the axis.

25. The apparatus of claim 1, wherein the planes are successively acquired.

* * * * *